United States Patent [19]

Bjornsson

[11] Patent Number: 5,424,040
[45] Date of Patent: Jun. 13, 1995

[54] TISSUE SPECIMEN COLLECTION KIT

[76] Inventor: Bjorn L. Bjornsson, 35 School St., Northborough, Mass. 01532

[21] Appl. No.: 92,929

[22] Filed: Jul. 15, 1993

Related U.S. Application Data

[63] Continuation-in-part of Ser. No. 973,843, Nov. 9, 1992, abandoned.

[51] Int. Cl.6 .............................................. B01L 11/00
[52] U.S. Cl. ...................... 422/101; 422/61; 422/99; 422/102; 422/104; 436/174; 436/176
[58] Field of Search .............. 425/256, 425, 435, 117, 425/127; 426/514, 515; 422/99, 101, 104, 102, 61; 436/174, 176, 808

[56] References Cited

U.S. PATENT DOCUMENTS

| | | | |
|---|---|---|---|
| 4,557,903 | 12/1985 | McCormick | 422/102 |
| 4,569,647 | 2/1986 | McCormick | 422/99 |
| 4,801,553 | 1/1989 | Owen et al. | 422/99 |
| 5,061,452 | 10/1991 | Yamamoto et al. | 425/117 |
| 5,080,869 | 1/1992 | McCormick | 422/107 |
| 5,219,525 | 6/1993 | Harrison | 422/101 |

OTHER PUBLICATIONS

Fisher Catalog 1986 pp. 1053, 1383, 1384.

Primary Examiner—Donald E. Czaja
Assistant Examiner—Lien Tran
Attorney, Agent, or Firm—Maryam Bani-Jamali

[57] ABSTRACT

A surgical pathological specimen kit with cassette. The kit includes a surgical cassette for receiving a pathological specimen, a conical guide for guiding the specimen into the cassette, a cylindrical container to house the cassette and conical guide, and a lid to close the cylindrical container and seal the cassette and conical guide from the exterior. The cassette has a permeable concave membrane which eliminates mechanical handling and increases tissue yield for microscopic examination. A bar code tracking or audit system is used to facilitate identification, tracking and storage of specimens and cassettes.

8 Claims, 8 Drawing Sheets

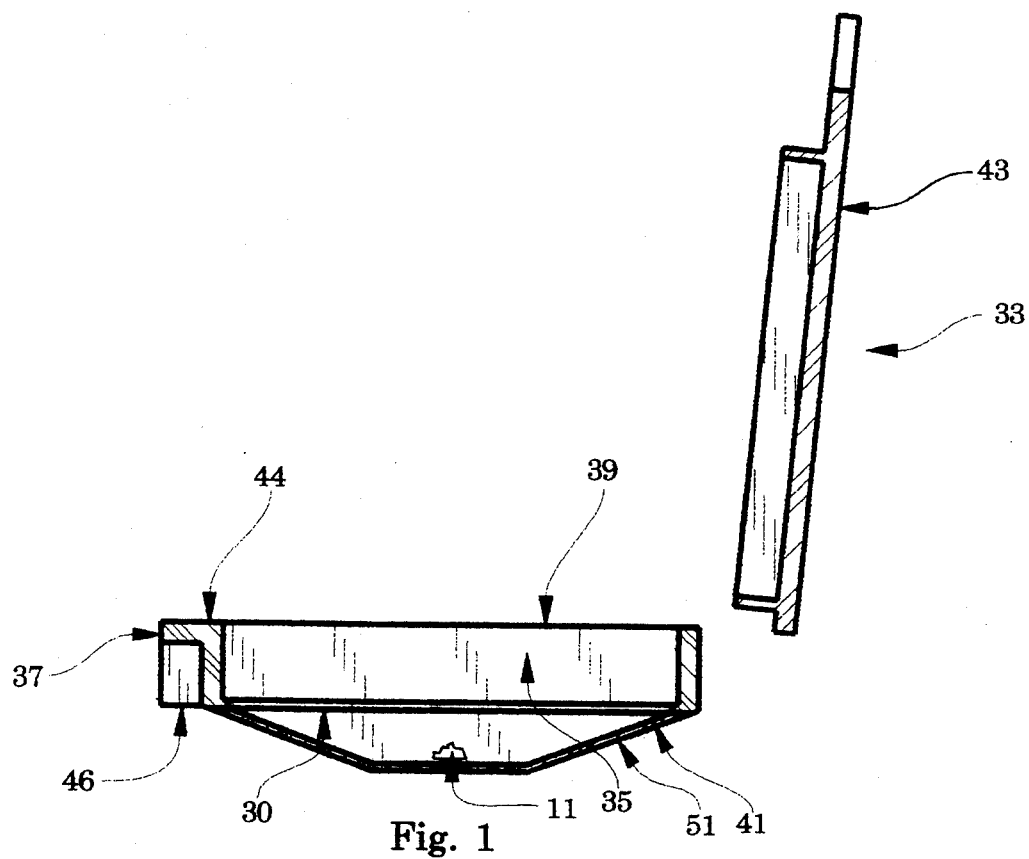
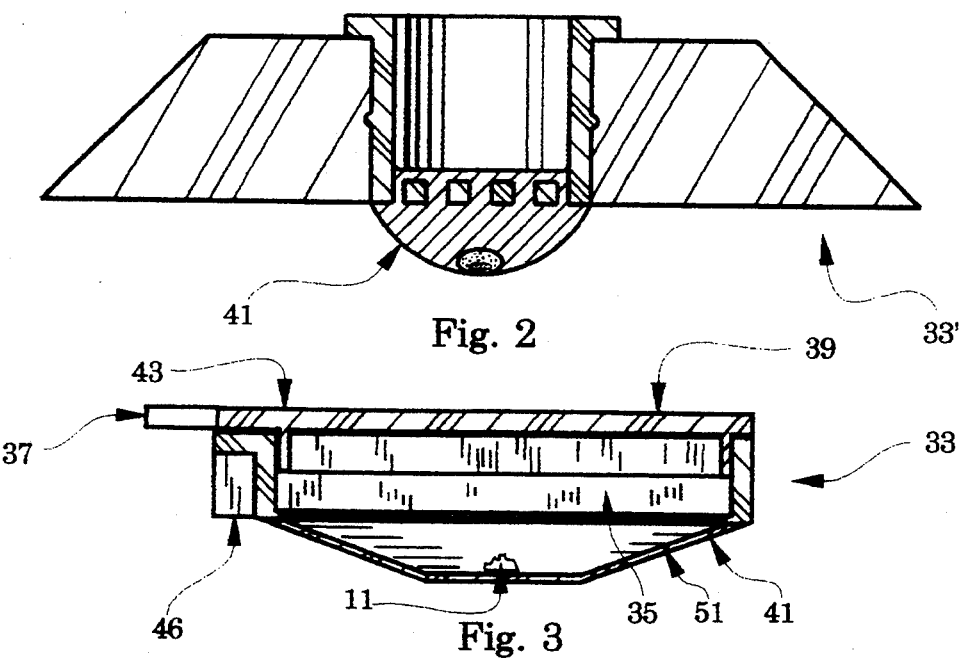

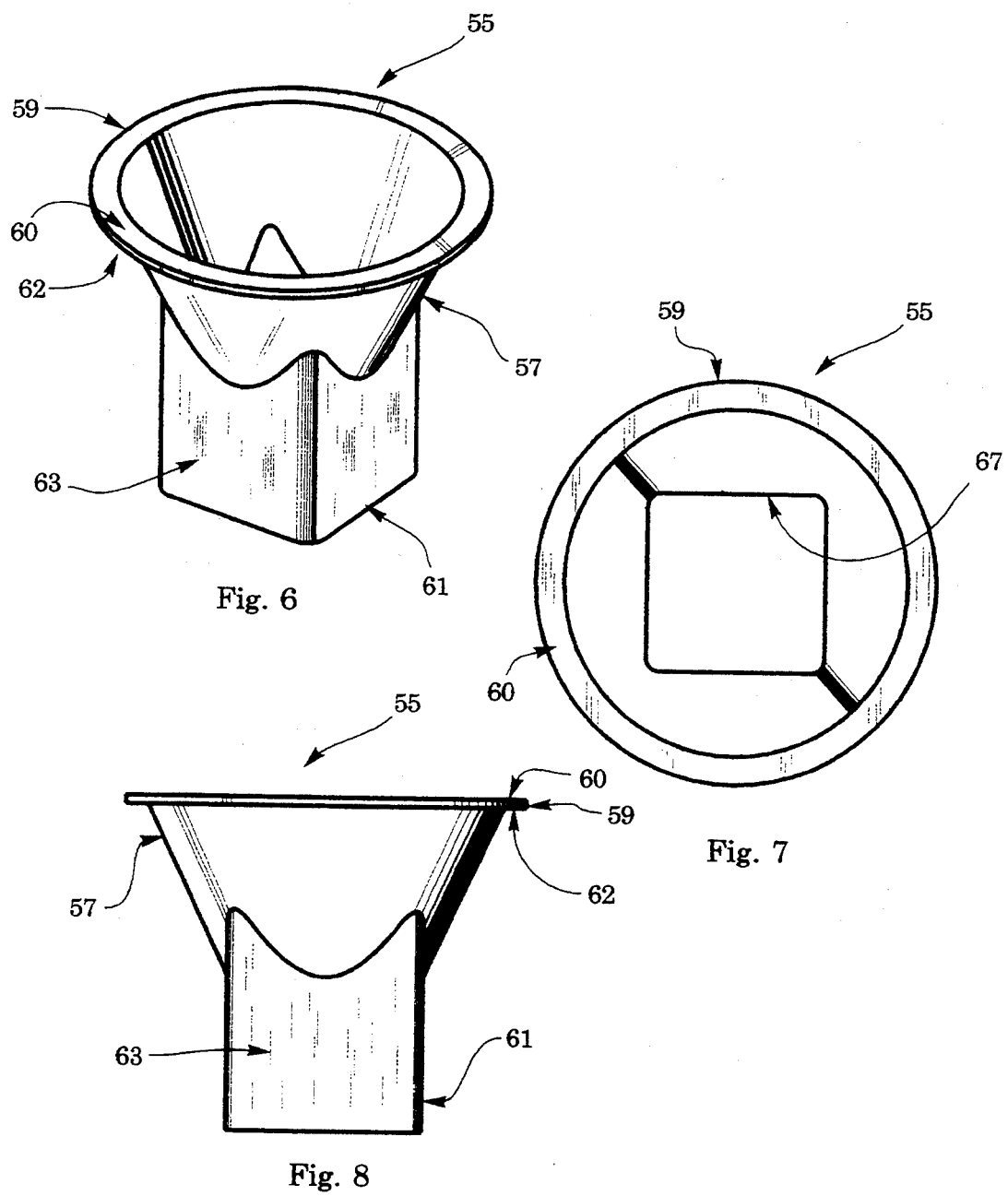

TISSUE SPECIMEN COLLECTION KIT

This is a continuation in part of application Ser. No. 07/973,843, filed on Nov. 9, 1992, now abandoned.

BACKGROUND OF THE INVENTION

The present invention is directed generally toward a tissue specimen collection kit with bar code process and audit system for tracking tissue specimens after biopsy.

With the advent of needle and fiberoptic biopsy techniques, tissue specimens have become smaller and more numerous. The tissue is increasingly difficult to recover from specimen jars and harder to preserve. The complicity of operating room routines and laboratory routines makes the probability of specimen mis-identification much higher than in the past. The routines for processing a tissue specimen generally follow a chronology beginning in the operating room and ending in a slide storage room.

Biopsy processing begins in the operating room when the physician excises the tissue from a patient and places it in a temporary storage container having a tissue preservative solution. Various storage containers may be used to temporarily hold the biopsied specimen while it is being prepared for transport for later analysis in the laboratory. The storage containers are usually identified by a patient identification number and name embossed on a label affixed to the side of the storage container. The specimen is listed in a log book in an area near the operating room and left for a person to transport it to the pathology lab. Such identification procedures often invite the possibility of mislabelling or mis-identification of specimens.

The specimen is next taken from the operating room area to a laboratory assistant's area where the specimen is logged into a centralized computer by entering the necessary identification information. Log-in procedures invite opportunity for error if original storage containers have previously been incorrectly labelled. The pathologist's assistant prepares and writes or embosses the identification information on a series of cassettes which will receive the specimen samples. Loose or empty cassettes left on the bench may be accidently swapped or confused with cassettes belonging to other cases.

Next, the pathologist's assistant removes the specimen from the container using a pair of forceps. These methods of specimen retrieval often increase the probability of incompletely recovering or fragmenting the biopsied specimen. Even if a Vabra or similar suction device is used to collect the specimen in the operating room, it is extremely hard to recover all of the tissue for processing. The assistant records and examines the specimen.

The tissue specimens are then placed on a sheet of filter paper which is either placed directly into the cassette or which is sandwiched between a set of thin sponges and then placed into the cassette. The cassette is closed and placed into a bucket of fixative to join other cassettes processed that day.

Cassettes are then carried to a chemical processing area where they are placed into a chemical processing machine. The machine starts its fully automated process which consists of a series of chemical baths and rinses. It completes its task in about three to about ten hours.

After chemical processing the cassettes and specimens are taken to an embedding station. The cassette number, tissue type and number of tissue fragments are matched with log sheet data. The sponges and filter paper are removed and a mold or molds for tissue embedding is selected according to tissue size and shape. This system is often labor intensive, involves risk of tissue loss, damage, misplacement or contamination and specimen identification error.

Molten paraffin or similar embedding medium is poured into the prepared molds. The tissue is oriented with forceps so that its surface will be adequately exposed for microtome cutting. After the specimen and embedding medium cool the specimen-cassette unit "block" is removed from the mold. The "block" is then secured to a microtome fixture in preparation for cross-sectional slicing. The flat "block" surface is exposed so that repeated incremental and cross-sectional slices of the tissue may be made. Commonly, the specimen cross-sections will be sliced either too thick or too thin by the microtome blade. Additional slices are generally necessary to attain correct cross-sectional slice thickness of embedding medium and specimen. Also, many times, repetitive slices are necessary to reach the specimen which is embedded deep within the embedding medium away from the hardened "blocks" surface. Such repetitive slicing will inevitably increase the wear on the microtome blade as well as compromise the precision of other cross-sectional slices processed later in the day. The string of cross-sectional slices are then placed on a water bath to remove any curling of specimen and paraffin caused by the cyclic slicing of the microtome.

After microtome cutting, the string of cross-sectional tissue-paraffin slices are individually placed on marked slides. The remaining paraffin or similar fixative is chemically removed and the specimens are stained and cover-slipped. The slides are then sent from the histopathology staining area to the pathologist for microscopic examination. The remaining slides and paraffin blocks are taken to a file room for storage.

Tissue specimen processing is fiddled with human errors and technical imperfections that significantly reduce the accuracy, efficiency and preservation of specimen. Such imperfections inevitably affect the accuracy of diagnosis by the pathologist. These and other difficulties experienced with the prior art devices have been obviated in a novel manner by the present invention.

It is therefore, an outstanding object of the invention to provide a tissue specimen collection kit which will remove human errors and technical imperfections which significantly reduce the efficiency and accuracy of diagnosis of tissue specimens.

A further object of the present invention is the provision of a tissue specimen collection kit which is simple in construction, which is inexpensive to manufacture and which will reduce amount of labor necessary for processing.

It is another object of the present invention to provide a tissue container which will allow for ease of retrieval of biopsied specimens.

A still further object of the invention is the provision of a bar coding system for ease of identification, tracking and storage of biopsied specimens.

It is a further object of the invention to provide a tissue cassette which will minimize tissue fragmentation or escape, almost eliminate specimen handling and increase tissue yield. It is a still further object of the present invention to provide a tissue cassette having a porous concave surface which will allow for maximum elevation of a specimen to the surface of an embedding "block" for improved cross-sectional slicing.

With these and other objects in view, as will be apparent to those skilled in the art, the invention resides in the combination of parts set forth in the specification and covered by the claims appended hereto.

SUMMARY OF THE INVENTION

In general, the invention consists of a tissue specimen collection kit with cassette. The kit includes a tissue cassette for receiving a tissue specimen, a guide member which is preferably conical in shape for guiding the specimen into the cassette, a container which is preferably cylindrical in shape to house the cassette and conical guide member and a lid to close the container and close the cassette and conical guide member from the exterior. The tissue cassette has a housing. The housing has a first end and a second end and interior and exterior faces. A concave membrane forms a bottom face of the tissue cassette and protrudes below the housing of the tissue cassette. The tissue cassette has a lid or stopper for closing the cassette.

The conical guide member has a spherical first end with a lip and a second end and an interior face and an exterior face, the second end being designed in such a way that the exterior face will engage the interior face of the housing of the tissue cassette and guide a tissue specimen to the center of the tissue cassette.

The container has a closed end and an open end. The open end of the container is designed to receive the conical guide member when the conical guide member and cassette are joined and inserted into the container.

The lid closes the container during transportation or storage.

BRIEF DESCRIPTION OF THE DRAWINGS

The character of the invention, however, may be best understood by reference to one of its structural forms, as illustrated by the accompanying drawings in which:

FIG. 1 is a right side elevation view of an embodiment of the tissue cassette;

FIG. 2 is a cross-sectional view showing a second embodiment of the cassette,

FIG. 3 is a right side elevation view of the same cassette with closed lid,

FIG. 6 is a perspective view of the conical guide member with a rectangular second end, FIG. 7 is a top plan view of the conical guide member showing an inward taper used to guide the specimen to the cassette, FIG. 8 is a front elevation view of the conical guide member.

DESCRIPTION OF THE PREFERRED EMBODIMENT

Figure 4:
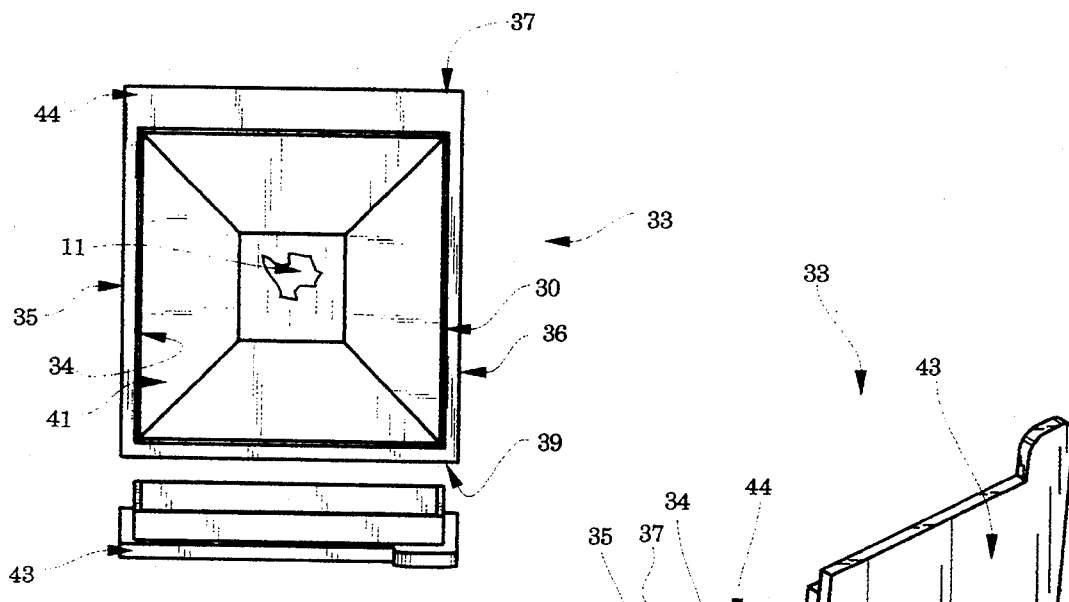
FIG. 4 is a top plan view of an embodiment of the cassette showing a housing design for receiving a second end of the conical guide member.

Referring first to FIGS. 1–12, the tissue specimen collection kit is generally indicated by the reference numeral 1 and comprises a tissue cassette as generally indicated by the reference numeral 33, a guide member which is most preferably conical in shape, as generally indicated by the reference numeral 55, a container which is most preferably cylindrical in shape, as generally indicated by the reference numeral 3, and a lid which is most preferably spherical in shape, as generally indicated by the reference numeral 29. The lid 29 may be replaced by a stopper indicated by the reference number 29''' as shown in FIG. 12C and FIG. 12D.

The cassette 33 as shown generally in FIGS. 1–5, further comprises a housing as generally indicated by the reference numeral 35, a concave bottom porous membrane 41, and a lid 43. The housing 35 has a top face 44 with an opening 38 and bottom face 46 as well as a first end 37 opposite a second end 39, and an interior face 34 and exterior face 36. A bottom porous membrane 41, which is most preferably concave or bubble-shaped and protrudes below the housing 35, 41 connects the first end 37 of the housing 35 to the second end 39 of the housing 35 and forms a part of the bottom face 46 of the cassette 33. The bottom porous membrane may be made of polypropylene, polycarbonate, or similar materials and may be attached to cassette 33 or 33' by heat welding, ultrasonic welding or other methods. The joining points of the housing 35 and bottom porous membrane 41 forms a ridge 30 on the interior face 34 of the housing 35 at approximately the mid-level of the cassette 33.

The conical guide member 55 of the tissue specimen kit 1 has a first end 57 and a second end 61 opposite the first end said second end 61 being preferably rectangular in shape. The first end 57 of conical guide member 55 has a protruding flat circular lip 59 around the perimeter of the first end 57 of the conical guide member 55. The protruding flat circular lip 59 has a top surface 60 and bottom surface 62 which gradually taper inward toward the second end 61 for guiding a specimen 11 toward the second end 61 and finally into an attached cassette 33. The second end 61 of the conical guide member 55 has an exterior face 63 and an interior face 67. The exterior face 63 is designed to engage the interior face 34 of the housing 35 and ridge 30 of the cassette 33 when the second end 61 is inserted into the cassette 33. A second embodiment of the conical guide member 55 may be used with cassette 33 or 33'. Conical guide member 55' has a funnel sheath 54. When inserted into the container 3, the funnel sheath 54 fits tightly against the container 3, such that when the guide member 55 and the attached cassette 33 or 33' are removed from the container 3, a relative vacuum is created in the container 3 below the bottom porous membrane 41, resulting in a drainage of solutions comprising fixatives through the porous membrane 41 back into the container 3. In another preferred embodiment, the cassette 33 or 33' may play the role of the conical guide member 55 or 55', fitting tightly against the container 3 in order to create a vacuum between the bottom porous membrane 41 and the container 3.

The container 3 of the specimen kit 1 has a housing 2 with a closed end 5 and an open end 7. Open end 7 of the container 3 has an inwardly projecting edge 9 to receive the lip 59 of the conical guide member 55 when the conical guide member 55 and cassette 33 are first joined together and then inserted into the container 3.

A lid 29 which is preferably spherical in shape is used to close the container 3 during a processing cycle and is designed so that it may screw onto the open end 7 of container 3. Spherical lid 29' is a second embodiment of the lid 29 and it is designed with a perimeter less than the open end 7 of the container 3 and may be inserted into the container 3 to rest upon the inwardly projecting edge 9 and close the container 3. The lid 29 and lid 29' each close the container 3 after the cassette 33 and conical guide member 55 are placed in the container 3. A stopper 29''' may be used to close cassette 33'. Stopper 29''' has a porous bottom wall which allows embedding material to harden above the bottom walls inside surface of stopper 29'''. Stopper 29''' becomes fixed in block 52 and acts as an anchor for porous membrane 41.

During operation of the invention the cylindrical container 3 of tissue specimen kit 1 may be present in an operating room. The container 3 may be used to collect a biopsied specimen 11 for later pathological analysis. The preferred embodiment of the present invention is designed to significantly simplify biopsy tracking and identification by providing a tissue cassette surface, which if labelled with a random bar code in the factory will be readable at time of specimen insertion in operating room, to be electronically matched with the identity of the patient so that tissue identification will be assured. An identical bar code number and indicia may be placed on container 3 of the tissue specimen collection kit 1.

After container 3 of tissue specimen kit 1, is taken from the pick-up area it will be brought to the pathologist's assistant's area. Conventional means generally requires the use of an assistant to enter indicia by a log-in procedure into a centralized computer. The present invention would instead use a bar code reader which would forward the indicia to the centralized computer. The indicia would be read from a bar code label set on the cassette by the manufacturer.

Figure 12A:
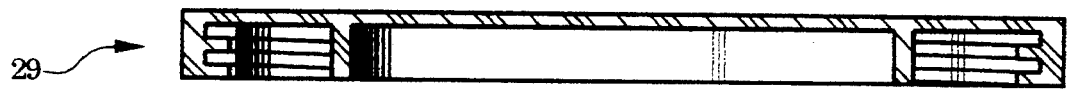
FIG. 12A is a cross-sectional view of one embodiment of a spherical lid used to close the container.
Figure 12B:
FIG. 12B is a cross-sectional view of a second embodiment of the spherical lid used to close the container.
Figure 12C:
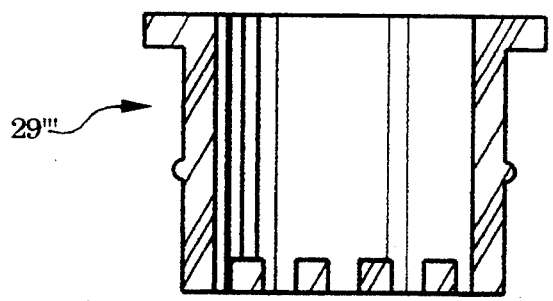
FIG. 12C is a cross-sectional view of a stopper used in place of a lid to close the cassette.
Figure 12D:
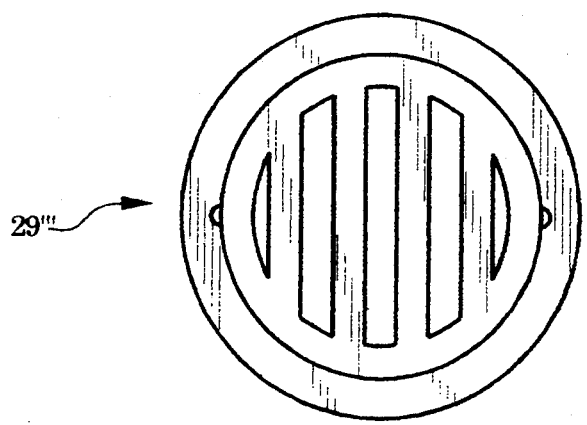
FIG. 12D is a bottom plan view of a stopper used to close the cassette.
Figure 13:
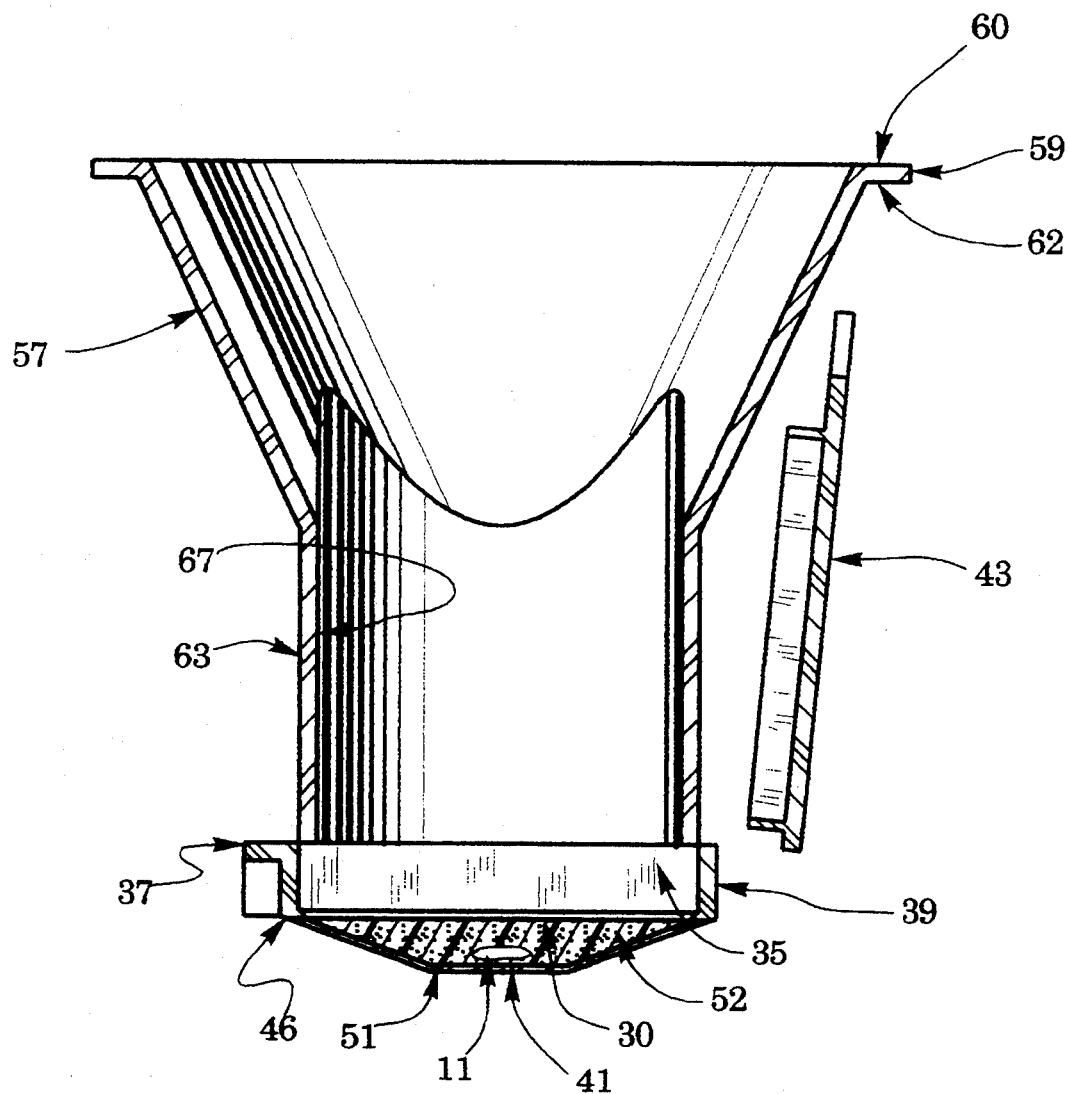
FIG. 13 is a front elevation view showing how the conical guide member engages the housing of the cassette.

The clear plastic design of the container lid 29 or 29' of the tissue specimen collection kit 1, as generally shown in FIG. 12A and 12B will allow the pathology lab assistant to determine the necessary number of cassettes 33 to house the biopsied specimen 11, without the need for opening or removing the tissue specimen 11 from the container 3. This allows for assurance of the presence of specimen 11 and omits the steps involved in opening the container with a pathologist's assistant breathing the noxious fumes from the enclosed tissue fixative.

In the next stage the specimen 11 is recovered from the container 3 of the tissue specimen collection kit 1.

Figure 14:
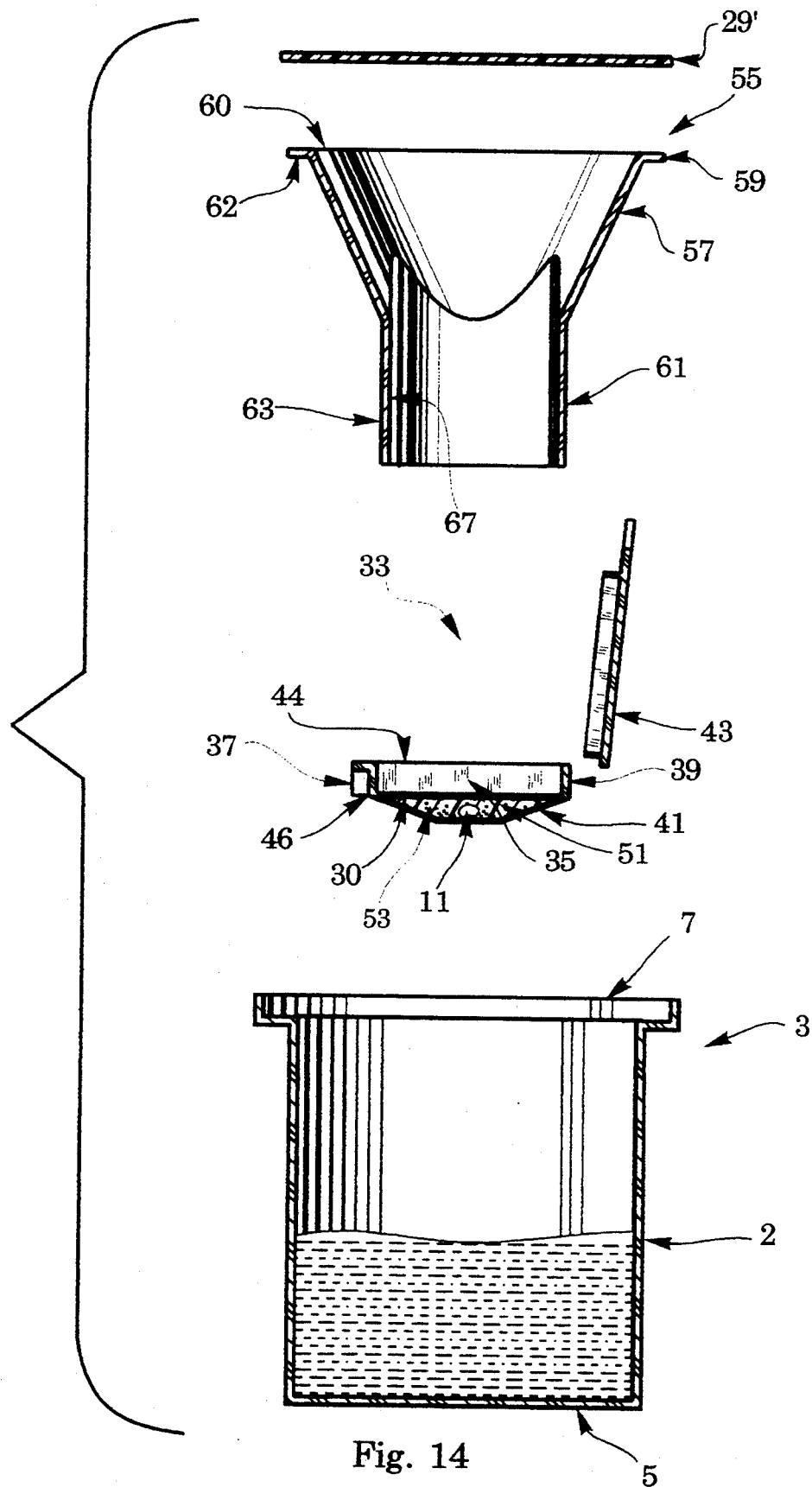
FIG. 14 is an exploded front elevation view of the cassette, conical guide member and the container and how the various kit parts are assembled.
Figure 15:
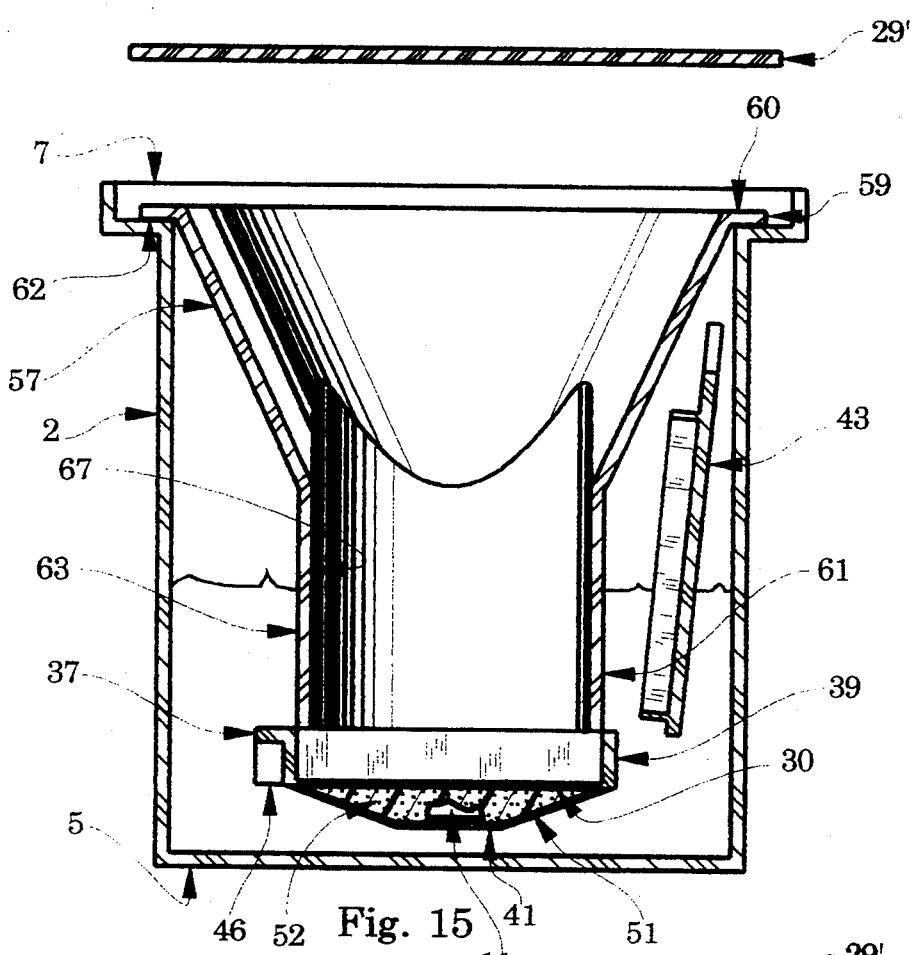
FIG. 15 shows a from elevation view of the cassette, conical guide member and container with a fixative added and no spherical lid attached.
Figure 16:
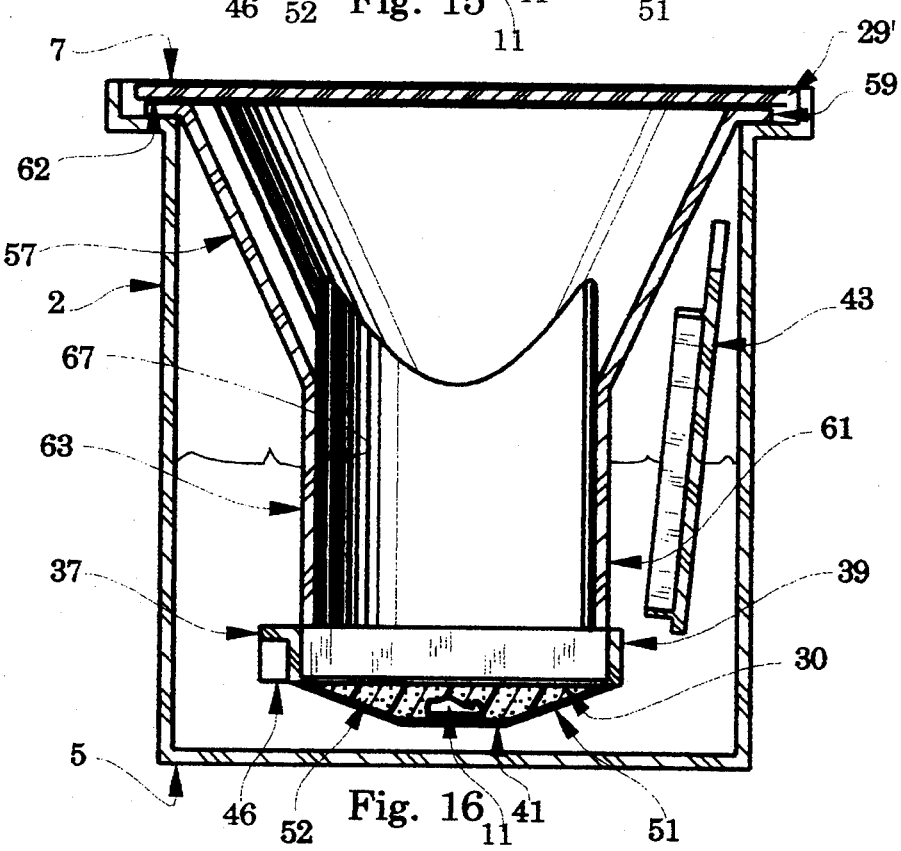
FIG. 16 shows a front elevation view of the cassette, conical guide member and container with the fixative added and a spherical lid closing the container.

Referring generally to FIGS. 14–16, the pathology assistant opens the container 3 by removing the container lid 29 or 29' and lifts the conical guide member 55 and attached cassette 33 of the tissue specimen collection kit 1, places it on a paper towel, detaches the conical guide member 55 from the surgical cassette 33 and discards the conical guide member 55 and the container 3. The specialized design of cassette 33 eliminates the need for the transfer of specimen 11 during subsequent examination. This eliminates problems of loss or trauma to specimen 11, or carry-over between specimens.

Figure 5A:
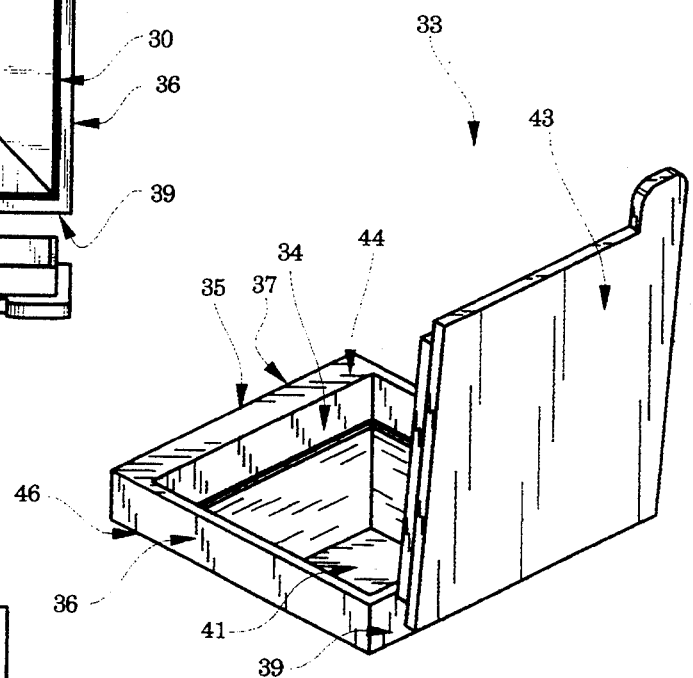
FIG. 5A is a perspective view of the cassette.
Figure 5B:
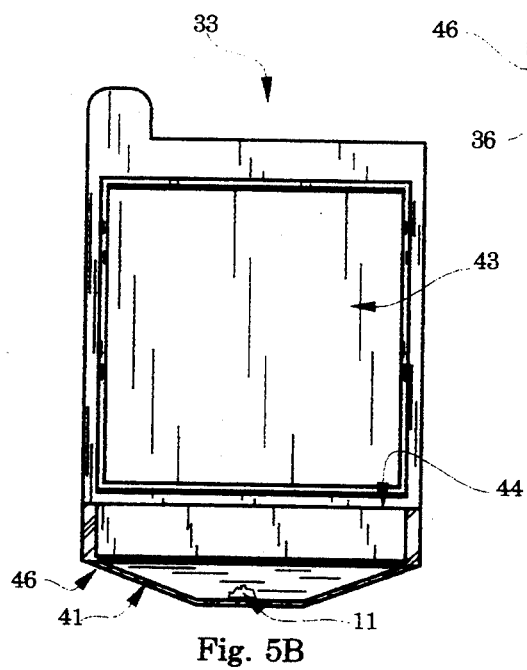
FIG. 5B is a front elevation view of the cassette with open lid.
Figure 9:
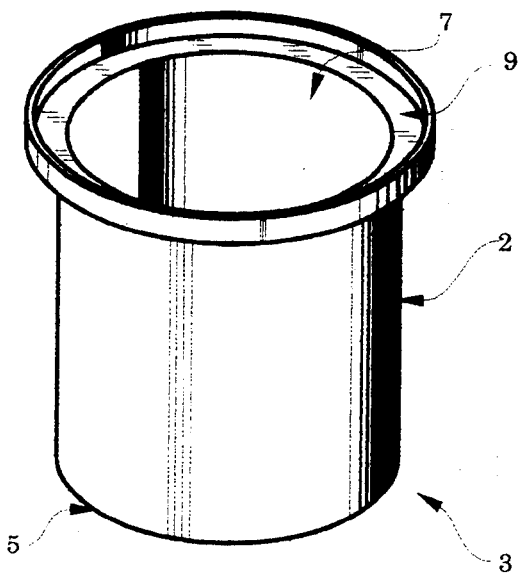
FIG. 9 is a perspective view of a container used to house the cassette and conical guide member.
Figure 10:
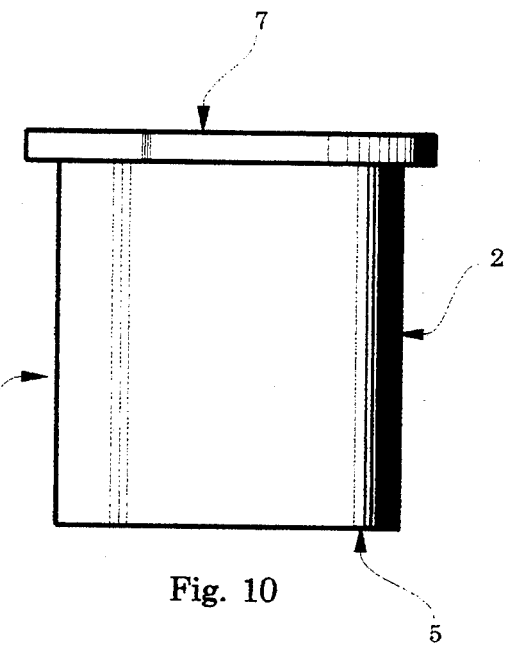
FIG. 10 is a front elevation view of the container.
Figure 11:
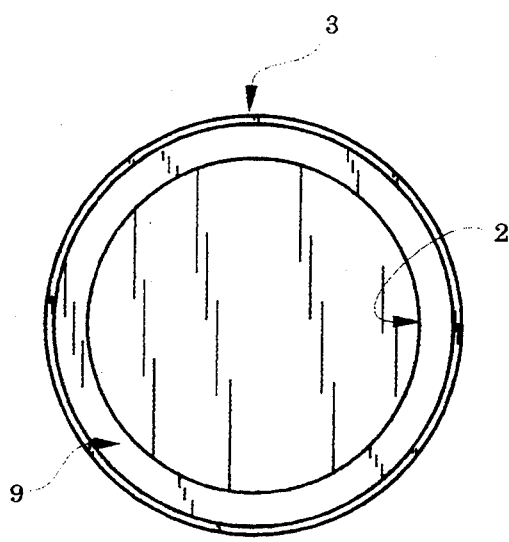
FIG. 11 is a top plan view of the container.

Referring now generally to FIGS. 5–7 the design of the cassette 33 eliminates the need for transfer of specimen 11. The existing method provides for use of sponges or filter paper to protect the sample during chemical processing. The bubble-shaped construction of the bottom porous membrane 41 is such that the pores 51 of the bottom porous membrane 41 are large enough to allow formalin or similar fixative to diffuse, but small enough to prevent the escape of fragments of specimen 11. The specialized design of the bottom porous membrane 41 also will decrease the risk of biopsy over-processing or over-drying during chemical processing.

After the cassettes 33 are chemically processed, they are taken to the embedding station. A bar code reader may be used for identification and tracking of bar coded cassettes. The design of cassette 33 of the tissue specimen collection kit 1 is such that no molds are necessary. Paraffin or similar embedding medium 53 is poured directly into cassette 33 filling it to about one-half level. The ridge 30 formed at the joining points of the housing 35 and the bottom porous membrane 41 will provide retaining points for the molten paraffin 53 poured into the cassette 33. The tissue cassette 33 need never be flipped over as conventional molds require. The bottom porous membrane 41 may then be peeled off cassette 33 to prepare the hardened paraffin "block" 52 for microtome cutting without any need for cleaning or recycling required of conventional molds. Additionally, the bottom porous membrane 41 in cassette embodiment 33' need never be removed. The whole cassette 33' may be placed directly on the microtome. The microtome blade slices through the bottom porous membrane 41. The bottom of stopper 29''' provides support for the block. A bar code reader may be used to identify the "block" and display the information on a computer terminal. Identification indicia may then be embossed on a microscopic slide before Histopathology staining. The bar coded blocks and slides provide for increased ease of storage and organization in the file room over the conventional art.

Clearly, minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A tissue specimen collection kit comprising:
 (a) a tissue cassette for receiving and holding a tissue specimen, said cassette comprising:
  (1) a housing said housing having a top face with art opening and a bottom face with an opening and interior and exterior faces between said top face and said bottom face for enclosing said tissue specimen,
(2) a bottom porous membrane which is removably mounted on said opening of said bottom face of said housing for holding said tissue specimen in said housing, said bottom porous membrane protruding below said housing,
(3) a lid for closing the opening of the top face of the housing of said tissue cassette,
(b) a conical guide member for guiding said specimen into said housing of said cassette, said guide member having an open first end and an open second end, said first end of said conical guide member located opposite said second end and having a diameter larger than said second end for guiding said tissue specimen toward said second end, said guide member comprising a cylindrical chamber with interior and exterior faces and said exterior face of said cylindrical chamber designed to engage the interior face of said tissue cassette, such that said tissue cassette is supported on said conical guide member, whereby when said specimen is passed through said open first end and then expelled by force of gravity from said open second end, said specimen will be directed through said cylindrical chamber of said guide member into said housing and onto said bottom porous membrane;
(c) a container with an open top end and a closed bottom end, said container having a compartment with a top open end and with a perimeter larger than the perimeter of said conical guide member and of said tissue cassette so that when the tissue cassette and the conical guide member are joined together they may be inserted into said compartment of said container, said container having a means for removably supporting said guide member on said container such that said guide member is located in said compartment; and
(d) a lid for closing the open top end of said container after said tissue cassette and said conical guide member are inserted into said container.

2. A tissue specimen collection kit as recited in claim 1, wherein said guide member is funnel shaped, wherein said guide member is inserted into said container, and wherein said guide member has a funnel sheath that fits tightly against the container, such that when the guide member and the attached cassette are removed from the container, a relative vacuum is created in the container below the bottom porous membrane, resulting in a drainage of solutions comprising fixatives through the porous membrane back into the container.

3. A tissue specimen collection kit comprising:
(a) a tissue cassette for receiving and holding a tissue specimen, said cassette comprising:
(1) a housing for enclosing said tissue specimen, said housing having a top face with an opening and a bottom face opposite said top face, interior and exterior faces between said top face and said bottom face, said bottom face comprising a first end and, a second end which are horizontal faces and a bottom porous membrane connecting said first end of said housing to said second end of said housing, said bottom porous membrane protruding below joining points of said membrane with said horizontal faces; and
(2) a lid for closing the opening of the top face of the housing of said tissue cassette.

(b) a conical guide member having interior and exterior faces and a circular open first end opposite an open second end, said first end having a protruding flat circular lip around the circumference of said first end which tapers inward toward said second end to guide said tissue specimen toward said second end, said exterior face of said second end designed to engage the interior face of said housing of said tissue cassette, said cassette being removably supported on said guide member so that a specimen is guided by force of gravity and by said guide member into said housing, and onto said bottom porous membrane;
(c) a cylindrical container with a closed bottom end and an open top end, said open top end having an inward projecting boundary to receive said lip of said conical guide member when said conical guide member and said tissue cassette are joined together and then inserted into said container, said container having a compartment with a top open end with a perimeter slightly larger than that of said conical guide member and that of said tissue cassette such that when said conical guide member and said tissue cassette are joined together, the cassette and the guide member can fit tightly in said compartment, said container including a means for removably supporting said guide member in said container; and
(d) a lid for closing the open top end of said cylindrical container after said tissue cassette and said conical guide member are inserted into said cylindrical container.

4. A tissue specimen collection kit for collecting and encasing a tissue specimen, comprising:
(a) a tissue cassette for receiving and holding a tissue specimen, said cassette comprising:
(1) a housing having a top boundary surrounding a top opening and a bottom face with an opening located opposite said top boundary, interior and exterior faces connecting said top boundary to said bottom face,
(2) a flexible, formed bottom porous membrane which is removably mounted on said housing for closing said opening of said bottom face, said bottom porous membrane protruding below said housing,
(3) a lid for closing the top opening of the housing of the cassette,
(b) a guide member having interior and exterior faces, and an open first end opposite an open second end, said first end having a protruding lip around said first end which tapers inward toward said second end to guide said tissue specimen toward said second end, said exterior face of said second end designed to engage the interior face of said housing of said tissue cassette, said cassette being removably supported on said guide member so that a specimen is guided by force of gravity and by said guide member into said housing, and onto said bottom porous membrane;
(c) a container with an open top and a closed bottom end, said open top end having a means for removably supporting said guide member when said guide member and said tissue cassette are first joined together and then inserted into said container, said container having an open top end with a perimeter larger than the perimeter of said guide member and of said tissue cassette such that when said guide member and said tissue cassette are joined together, the cassette and the guide member can fit in said container; and (d) a lid for closing said open top end of said container after said tissue cassette and said guide member are inserted into said container.

5. A tissue specimen collection kit for collecting and encasing a tissue specimen, comprising:

(a) a tissue cassette for receiving and holding a tissue specimen, said tissue cassette comprising:

(1) a housing for enclosing said tissue specimen, said housing having a top boundary surrounding a top opening and a bottom face located opposite said top boundary, interior and exterior faces connecting said top boundary to said bottom face, said bottom face comprising a first end and a second end which are horizontal faces and a bottom porous membrane, said bottom porous membrane connecting the first end of said housing to the second end of said housing, and said bottom porous membrane protruding below joining points of said membrane with said horizontal faces, (2) a perforated lid for closing the top opening of the housing of said tissue cassette, (b) a funnel-shaped guide member having interior and exterior faces and an open first end and an open second end which is opposite said open first end, said open first end being substantially larger than said open second end, said first end having a protruding lip around the perimeter of said first end which gradually tapers inward toward said second end to guide said tissue specimen toward said second end, said exterior face of said second end designed to engage the interior face of said housing of said tissue cassette such that the specimen is guided by said guide member and by force of gravity into said cassette;

(c) a container having an open top end and a closed bottom end, said open top end having a perimeter larger than the perimeter of said guide member and of said tissue cassette such that said container is able to receive and removably support said lip of said guide member when said guide member and said tissue cassette are first joined together and then inserted into said container; and (d) a lid for closing said open top end of said container after said cassette and said guide member are inserted into said container.

6. A tissue specimen collection kit as recited in claim 5, wherein said container has interior faces, and wherein said guide member has a funnel sheath that fits tightly against the interior faces of the container, such that when removed with attached cassette from the container, it will create a relative vacuum in the container below the bottom porous membrane and cause a drainage of solutions comprising fixatives through the porous membrane back into the container.

7. A tissue specimen collection kit as recited in claim 6, wherein said open first end of the guide member matches any shape that the open top end of the container has and the open second end of the guide member matches any shape that the top boundary of the housing has.

8. A tissue specimen collection kit comprising:

(a) a tissue cassette for receiving and holding a tissue specimen, said cassette comprising:

(1) a housing for enclosing said tissue specimen with a top boundary surrounding a top opening, a bottom boundary surrounding a bottom opening, said bottom boundary located opposite said top boundary, and interior and exterior faces interposed between said top boundary and said bottom boundary, (2) a flexible, formed bottom porous membrane which is removably mounted on said bottom boundary of said housing for closing said bottom opening of said housing, said bottom porous membrane protruding below said bottom boundary of said housing, (3) a lid for closing the top opening of the housing of said tissue cassette, (b) a guide member having interior and exterior faces and a first end with a perimeter and a protruding lip around the perimeter of said first end which tapers inward toward a second end to guide said tissue specimen toward said second end, said exterior face of said second end designed to engage the interior face of said housing of said tissue cassette in a tight fit;

(c) a container art open top end and a closed bottom end, said open top end having a boundary to receive and removably support said protruding lip of said guide member when said guide member and said tissue cassette are first joined together and then inserted into said container; and (d) a lid for closing the open top end of said container after said tissue cassette and said guide member are inserted into said container.

* * * * *